United States Patent
Omura et al.

(10) Patent No.: US 10,792,235 B2
(45) Date of Patent: Oct. 6, 2020

(54) TRANSPARENT OILY SOLID COSMETICS

(71) Applicant: Kokyu Alcohol Kogyo Co., Ltd., Narita-shi, Chiba (JP)

(72) Inventors: Takayuki Omura, Narita (JP); Nana Arahira, Narita (JP); Kiyotaka Kawai, Narita (JP)

(73) Assignee: Kokyu Alcohol Kogyo Co., Ltd., Narita-shi, Chiba (JP)

( * ) Notice: Subject to any disclaimer, the term of this patent is extended or adjusted under 35 U.S.C. 154(b) by 0 days.

(21) Appl. No.: 15/823,688

(22) Filed: Nov. 28, 2017

(65) Prior Publication Data
US 2018/0344601 A1    Dec. 6, 2018

(30) Foreign Application Priority Data
May 30, 2017    (JP) .................. 2017-106401

(51) Int. Cl.
| | | |
|---|---|---|
| *A61K 8/42* | (2006.01) | |
| *A61K 8/37* | (2006.01) | |
| *A61K 8/44* | (2006.01) | |
| *A61Q 17/04* | (2006.01) | |
| *A61Q 1/06* | (2006.01) | |
| *A61K 8/365* | (2006.01) | |
| *A61K 8/36* | (2006.01) | |
| *A61Q 1/00* | (2006.01) | |
| *A61Q 5/06* | (2006.01) | |
| *A61Q 1/04* | (2006.01) | |

(52) U.S. Cl.
CPC ............. *A61K 8/42* (2013.01); *A61K 8/361* (2013.01); *A61K 8/365* (2013.01); *A61K 8/37* (2013.01); *A61K 8/442* (2013.01); *A61Q 1/00* (2013.01); *A61Q 1/06* (2013.01); *A61Q 5/06* (2013.01); *A61Q 17/04* (2013.01); *A61K 2800/10* (2013.01); *A61K 2800/262* (2013.01); *A61K 2800/592* (2013.01); *A61Q 1/04* (2013.01)

(58) Field of Classification Search
None
See application file for complete search history.

(56) References Cited

U.S. PATENT DOCUMENTS

| | | |
|---|---|---|
| 7,244,419 B2 | 7/2007 | Yamato et al. |
| 2009/0280076 A1 * | 11/2009 | Yoshida ............ A61K 8/442 424/59 |
| 2012/0039972 A1 | 2/2012 | Kobayashi et al. |
| 2016/0331661 A1 | 11/2016 | Masuno et al. |

FOREIGN PATENT DOCUMENTS

| | | | |
|---|---|---|---|
| EP | 1905411 A1 | 4/2008 | |
| EP | 2298274 A1 | 3/2011 | |
| EP | 3098216 A1 * | 11/2016 | ............ A61K 8/37 |
| JP | H01163111 A | 6/1989 | |
| JP | 2001-172128 A | 6/2001 | |
| JP | 4174994 B2 | 11/2008 | |
| JP | 5117004 B2 | 1/2013 | |
| JP | 5663111 B1 | 2/2015 | |
| JP | 5759721 B2 | 8/2015 | |
| KR | 2014-0031503 A | 3/2014 | |
| KR | 10-1727027 B1 | 4/2017 | |
| WO | WO 2009/139092 A1 | 11/2009 | |
| WO | WO 2010/128639 A1 | 11/2010 | |
| WO | WO-2015108176 A1 * | 7/2015 | ............ A61K 8/37 |
| WO | WO 2018/079568 A2 | 5/2018 | |

OTHER PUBLICATIONS

[No Author Listed] Canmake Your Lip Only Balm. Cosmetic-Info.jp. Aug. 2, 2016.
Arahira et al., A new ingredient appropriate for lip tint formulations. Fragrance J. Apr. 2017. 29-34.
[No Author Listed] Database GNPD Mintel. Crystal Lip Balm. Apr. 30, 2010.
[No Author Listed] Database GNPD Mintel. Full Moon Party Lip Care. May 31, 2016.
[No Author Listed] Database GNPD Mintel. Lips Crystal. Jan. 31, 2017.
[No Author Listed] Database GNPD Mintel. Licks Lip Balms. Jul. 31, 2001.
[No Author Listed] Database GNPD Mintel. Juicy Jelly Green Apple Lip Balm. Dec. 31, 2015.
[No Author Listed] Database GNPD Mintel. Lipstick. Mar. 31, 2017.
Saito et al., Fragrance J. 2007. 35(7):60-65.

* cited by examiner

*Primary Examiner* — James W Rogers
(74) *Attorney, Agent, or Firm* — Wolf, Greenfield & Sacks, P.C.

(57) ABSTRACT

The present invention relates to a transparent oily solid cosmetic having excellent transparency, no bleeding, and excellent usability.
[Problem]
It has been difficult to produce an oily solid cosmetic having both excellent transparency and low bleeding by merely combining conventional materials.
[Solution]
A transparent oily solid cosmetic comprising a transparent gelling agent, an oil agent having a refractive index of 1,460 or more at 20° C., and an oil agent having an expansion coefficient of 0.065%/° C. or less. In particular, a transparent oily solid cosmetic wherein the transparent gelling agent comprises dibutyl lauroyl glutamide and/or dibutyl ethylhexanoyl glutamide.

8 Claims, No Drawings

TRANSPARENT OILY SOLID COSMETICS

TECHNICAL FIELD

The present invention relates to an oily solid cosmetic.

BACKGROUND ART

Conventionally, oily solid cosmetics having various physical properties have been researched and developed according to each application and purpose.

Patent Document 1 discloses a cosmetic containing dibutyl lauroyl glutamide (GP-1) and dibutyl ethylhexanoyl glutamide (EB-21) as an amino-acid based gelling agent and a polyamide resin; it describes that the brittleness of cosmetic products which use a single amino-acid based gelling agent can be improved by the combination with a polyamide resin, and therefore cosmetic products having excellent usability and storage stability can be provided.

In addition, Patent Document 2 discloses a gelling agent made by mixing dibutyl lauroyl glutamide (GP-1) and dibutyl ethylhexanoyl glutamide (EB-21), and describes that this gelling agent is a gelling agent capable of producing a gel-like composition having excellent gel strength and transparency.

Also, Patent Document 3 discloses an ester compound of tricyclo [$5.2.1.0^{2,6}$] decane, and describes that this is a compound having excellent anti-bleeding power and usability.

In addition, Patent Document 4 discloses a transparent stick-type ultraviolet-blocking cosmetic composition containing a polyamide based gelling agent, an amino-acid based gelling agent, and an organic sunscreen and oil; specifically, bisalkyl (C14-18) amide (ethylene diamine/ hydrogenated dimer dilinoleate) copolymer is used as a polyamide gelling agent, and dibutyl ethylhexanoyl glutamide and dibutyl lauroyl glutamide are used as an amino-acid based gelling agent.

In addition, Patent Document 5 discloses an oily composition containing an N-acyl amino acid derivative such as dibutyl lauroyl glutamide (GP-1) and dibutyl ethylhexanoyl glutamide (EB-21), a polyamide resin and a liquid oil, which becomes a rod-like preparation for the lips after solidification.

However, there is no oily solid cosmetic which is satisfactory enough in each respect of excellent transparency, no bleeding due to aging, and excellent storage stability.

CITATION LIST

Patent Document

[Patent Document 1] JP No. 5759721
[Patent Document 2] JP No. 4174994
[Patent Document 3] JP No. 5663111
[Patent Document 4] Korean registered patent No. 1020140031503
[Patent Document 5] WO 2010/128639

SUMMARY OF THE INVENTION

Problems to be Solved by the Invention

Therefore, an object of the present invention is to provide a transparent oily solid cosmetic having excellent transparency and no bleeding. Another object of the present invention is to provide an oily solid cosmetic having excellent usability.

Means of Solving the Problems

In investigating to solve the above-mentioned problems, the present inventors have faced a problem that it is difficult to produce an oily solid cosmetic which can achieve both excellent transparency and low bleeding by appropriately selecting conventional materials. As a result of further investigations to solve such problems, the present inventors have found that, by combining an oil agent having a high refractive index and an oil agent having a low expansion coefficient for a transparent gelling agent, it is possible to obtain an oily solid cosmetic having high transparency and low bleeding, and have completed the present invention.

Namely, the present invention relates to the following.

[1] A transparent oily solid cosmetic comprising a transparent gelling agent, an oil agent having a refractive index of 1.460 or more at 20° C., and an oil agent having an expansion coefficient of 0.065%/° C. or less.

[2] The transparent oily solid cosmetic according to [1], wherein the transparent gelling agent comprises dibutyl lauroyl glutamide and/or dibutyl ethylhexanoyl glutamide.

[3] The transparent oily solid cosmetic according to [2], wherein the content of dibutyl lauroyl glutamide is 2.0-7.0 wt %.

[4] The transparent oily solid cosmetic according to [2] or [3], wherein the content of dibutyl ethylhexanoyl glutamide is 0.5-5.0 wt %.

[5] The transparent oily solid cosmetic according to any one of [1] to [4], further comprising isostearic acid.

[6] The transparent oily solid cosmetic according to any one of [1] to [5], wherein the content of the oil agent having a refractive index of 1.460 or more at 20° C. is 20-80 wt %.

[7] The transparent oily solid cosmetic according to any one of [1] to [6], wherein the content of the oil agent having an expansion coefficient of 0.065 or less is 10-50 wt %.

[8] The transparent oily solid cosmetic according to any one of [1] to [7], further comprising 12-hydroxystearic acid.

[9] The transparent oily solid cosmetic according to [8], wherein the content of 12-hydroxystearic acid is 2.0-10.0 wt %.

[10] The transparent oily solid cosmetic according to any one of [1] to [9], wherein the oil agent having a refractive index of 1.460 or more at 20° C. is tricyclodecanemethyl isononanoate.

[11] The transparent oily solid cosmetic according to any one of Claims [1] to [10], wherein the oil agent having an expansion coefficient of 0.065 or less is isotridecyl isononanoate or isodecyl neopentanoate.

[12] The transparent oily solid cosmetic according to any one of [1] to [11], wherein the ingredient ratio in wt % between the oil agent having a refractive index of 1.460 or more at 20° C. and the oil agent having an expansion coefficient of 0.065 or less is from 10:1 to 1:1.

Advantageous Effects of the Invention

By means of a transparent gelling agent and a combined oil agent comprising an oil agent having a high refractive index and an oil agent having a low expansion coefficient, the present invention can provide a new transparent oily solid cosmetic used in oily solid cosmetics such as lipstick, hair chic and sun care products, which has excellent transparency, no bleeding and high storage stability, and is easy to spread with little stickiness and good usability. Although the mechanism for high transparency and low bleeding effects by a combined oil agent of an oil agent having high refractive index and an oil agent having low expansion coefficient is not necessarily clear, it is presumed that the characteristic of being not easily influenced by the temperature possessed by the oil agent having low expansion coefficient, is related to the low bleeding property.

The present invention makes it possible to produce a transparent oily solid cosmetic having high storage stability and exhibiting intended effects, as long as said oil agent is contained in an amount required as an oily solid cosmetic.

In particular, by selecting an oil agent having a refractive index of 1.460 or more at 20° C. and an oil agent having an expansion coefficient of 0.065 or less of the present invention and using them in combination, a transparent and low-bleeding high-quality cosmetic is provided. Needless to say, a single oil agent may be used as long as it is an oil agent that simultaneously satisfies the conditions of such refractive index and expansion coefficient.

DETAILED DESCRIPTION OF THE INVENTION

Hereinafter, the present invention will be described in detail based on preferred embodiments of the present invention.

The transparent oily solid cosmetic of the present invention is a cosmetic used for the body, face, hair, etc.

In the present invention, "solid cosmetic" is a cosmetic which can maintain a solid shape at room temperature (25° C.).

In the present invention, "cosmetic" is a material that can be used for the production of body care products, skin care products, makeup products, hair care products, fragrance products and the like, although not particularly limited thereto.

Body care products include, but are not limited to, UV care products, deodorant products, skin care products for the body, fragrance products for the body, cleansing products for the body and the like.

Skin care products include, but are not limited to, cleansing products, face washings, whitening cosmetic products, UV care cosmetic products, anti-aging products and the like.

Makeup products include, but are not limited to, foundation, lip color, lipstick, lip cream, eyeliner and the like.

Hair care products include, but are not limited to, hair styling wax, hair chic, hair treatment agent, one-day hair coloring agent, hair gloss and the like.

Fragrance products include, but are not limited to, perfume, eau de toilette, eau de cologne, eau de perfum, roll-on type fragrance, stick type paste perfume and the like.

In the present invention, the term "transparent" means that a solid cosmetic is not completely opaque, and the case where the transmittance is 60% or more described later is defined to be good transparency.

Table 1 below shows expansion coefficient of oil agents used in the cosmetics industry.

TABLE 1

| PRODUCT NAME | INCI NAME | VISCOSITY (mPa · s, 25° C.) | EXPANSION COEFFICIENT (%/° C.) |
| --- | --- | --- | --- |
| NEOLIGHT 100P | ISODECYL NEOPENTANOATE | 4 | 0.062 |
| KAK 99 | ISONONYL ISONONANOATE | 10 | 0.057 |
| ES108109 | ETHYLHEXYL ISONONANOATE | 10 | 0.054 |
| KAK 139 | ISOTRIDECYL ISONONANOATE | 11 | 0.053 |
| NEOLIGHT 180P | ISOSTEARYL NEOPENTANOATE | 14 | 0.080 |
| HICALL K-230 | MINERAL OIL | 20 | 0.078 |
| TCG-M | CAPRYLIC/CAPRIC TRYGLYCERIDE | 26 | 0.082 |
| ODM | OCTYLDODECYL MYRISTATE | 26 | 0.080 |
| TOG | TRIETHYLHEXANOIN | 31 | 0.081 |
| KAK TCIN | TRYCYCLODECANEMETHYL ISONONANOATE | 44 | 0.078 |
| RISONOL 20SP | OCTYLDODECANOL | 49 | 0.080 |
| RISOCAST IOHS | ETHYLHEXYL HYDROXYSTEARATE | 55 | 0.111 |
| RISOCAST ODSHS | OCTYLDODECYL STEAROYL STEARATE | 96 | 0.077 |
| KAK DADIP-R | DIISOPROPYL DIMER DILINOLEATE | 111 | 0.077 |
| TISG | TRIISOSTEARIN | 163 | 0.075 |
| KAK TTI | TRIMETHYLOLPROPANE TRIISOSTEARATE | 205 | 0.074 |
| RISOREX PGIS23 | POLYGLYCERYL-2 TRIISOSTEARATE | 339 | 0.075 |
| RISOREX PGIS22 | POLYGLYCERYL-2 DIISOSTEARATE | 577 | 0.075 |
| HAILUCENT DPIN6 | DIPENTAERYTHRITYL HEXAISONONANOATE | 1215 | 0.072 |
| HAIMALATE DIS | DIISOSTEARYL MALATE | 2574 | 0.076 |

As described above, the expansion coefficient of many oil agents used in the cosmetics industry is usually about 0.07-0.08%/° C.; whereas in the present invention, we focused on oil agents having an expansion coefficient of 0.065%/° C. or less, and found that bleeding can be suppressed by using these oil agents. This is considered to be attributed to the fact that the oil agents having a low expansion coefficient are hardly affected by temperature, so that bleeding could be suppressed. Furthermore, in order to solve a further problem that transparency cannot be maintained only by using an oil agent having an expansion coefficient of 0.065%/° C. or less, we have conducted further research and found that, by using an oil agent having a high refractive index, specifically a refractive index of 1.460 or more at 20° C., preferably an oil agent having a refractive index of more than 1.460, more preferably an oil agent having a refractive index of 1.465 or more, most preferably an oil agent having a refractive index of 1.470 or more, it is possible to obtain a solid cosmetic which maintains high transparency and has low bleeding and good storage stability; and we have thus completed the present invention.

Moreover, by adding 12-hydroxystearic acid, a transparent solid cosmetic showing grater suppression of bleeding was obtained.

The refractive index at 20° C. in the present invention was measured using RXA-170 from Anton Paar.

The following Table 2 shows the refractive index at 20° C. of oil agents used in the cosmetic industry.

TABLE 2

| PRODUCT NAME | INCI NAME | REFRACTIVE INDEX(20° C.) |
|---|---|---|
| HYDROGENATED POLYISOBUTENE (MW: 1000) | HYDROGENATED POLYISOBUTENE | 1.494 |
| KAK TCIN | TRICYCLODECANEMETHYL ISONONANOATE | 1.479 |
| HAILUCENT ISDA | POLYGLYCERYL-2 ISOSTEARATE/DIMER DILINOLEATE COPOLYMER | 1.479 |
| RISOCAST HSDA | DIGLYCERIN/DILINOLEIC ACID HYDROSTEARIC ACID COPOLYMER | 1.478 |
| RISOCAST DA-L | HYDROGENATED CASTOR OIL DIMER DILINOLEATE | 1.475 |
| RISOREX PGIS32 | POLYGLYCERYL-3 DIISOSTEARATE | 1.472 |
| RISOREX PGIS21 | POLYGLYCERYL-2 ISOSTEARATE | 1.470 |
| KAK PTI | PENTAERYTHRITYL TETRAISOSTEARATE | 1.468 |
| RISOREX PGIS22 | POLYGLYCERYL-2 DIISOSTEARATE | 1.468 |
| RISOCAST MIS | HYDROGENATED CASTOR OIL ISOSTEARATE | 1.468 |
| KAK TTI | TRIMETHYLOLPROPANE TRIISOSTEARATE | 1.467 |
| RISOREX PGIS23 | POLYGLYCERYL-2 TRIISOSTEARATE | 1.467 |
| ECO OIL RS | JOJOBA SEED OIL | 1.466 |
| KAK DADIP-R | DIISOPROPYL DIMER DILINOLEATE | 1.465 |
| TISG | TRIISOSTEARIN | 1.465 |
| LIQUID PARAFFIN (70 sec.) | MINERAL OIL | 1.464 |
| OLEYL ALCOHOL VP | OLEYL ALCOHOL | 1.463 |
| RISOCAST ODSHS | OCTYLDODECYL STEAROYL STEARATE | 1.460 |
| HAIMALATE DIS | DIISOSTEARYL MALATE | 1.460 |
| ISIS | ISOSTEARYL ISOSTEARATE | 1.458 |
| HAILUCENT DPIN6 | DIPENTAERYTHRITYL HEXAISONONANOATE | 1.458 |
| ICIS | HEXYLDECYL ISOSTEARATE | 1.457 |
| ISOSTEARYL ALCOHOL EX | ISOSTEARYL ALCOHOL | 1.457 |
| RISONOL 24SP | DECYLTETRADECANOL | 1.457 |
| RISOCAST IOHS | ETHYLHEXYL HYDROXYSTEARATE | 1.456 |
| ISOSTEARIC ACID EX | ISOSTEARIC ACID | 1.456 |
| ODM | OCTYLDODECYL MYRISTATE | 1.454 |
| ICS-R | ISOCETYL STEARATE | 1.454 |
| RISONOL 20SP | OCTYLDODECANOL | 1.454 |
| OLIVE SQUALANE | SQUALANE | 1.453 |
| ICM-R | ISOCETYL MYRISTATE | 1.453 |
| RISONOL 18SP | ISOSTEARYL ALCOHOL | 1.452 |
| KAK IBIS | ISOBUTYL ISOSTEARATE | 1.446 |
| KAK 139 | ISOTRYDECYL ISONONANOATE | 1.445 |
| ES108109 | ETHYLHEXYL ISONONANOATE | 1.436 |

As the oil agent having a refractive index of 1.460 or more at 20° C. in the present invention, without limitation, polyglyceryl-2 isostearate, polyglyceryl-3 diisostearate, hydrogenated castor oil dimer dilinoleate, (diglycerin/dilinoleate/hydroxystearate) copolymer, (polyglyceryl-2 isostearate/dimer dilinoleate) copolymer, tricyclodecanemethyl isononanoate, hydrogenated triisobutene, octyldodecyl stearoyloxy stearate, diisostearyl malate, oleyl alcohol, mineral oil, triisostearin, diisopropyl dilinoleate, jojoba seed oil, polyglyceryl-2 triisostearate, trimethylolpropane triisostearate, hydrogenated castor oil isostearate, polyglyceryl-2 diisostearate, pentaerythrityl tetraisostearate can be used; preferably, polyglyceryl-2 isostearate, polyglyceryl-3 diisostearate, hydrogenated castor oil dimer dilinoleate, (diglycerin/dilinoleate/hydroxystearate) copolymer, (polyglyceryl-2 isostearate/dimer dilinoleate) copolymer, tricyclodecanemethyl isononanoate, hydrogenated triisobutene can be used; and most preferably, tricyclodecanemethyl isononanoate can be used.

The content of the oil agent having a refractive index of 1.460 or more at 20° C. is preferably 20-80 wt %, more preferably 25-80 wt %, and most preferably 30-80 wt %.

In addition, the refractive index at 20° C. of the oil agent having a refractive index of 1.460 or more at 20° C. is preferably more than 1.460, more preferably 1.465 or more, and still more preferably 1.470 or more.

Regarding the expansion coefficient in the present invention, specific volume (m$^3$/kg) at a liquid temperature of 10-50° C. is measured using a vibration-type density meter DMA-4500M from Anton Paar, and the expansion coefficient per 1° C. is expressed in the unit of %/° C.

The oil agent having an expansion coefficient of 0.065%/° C. or less in the present invention is not limited, and ethylhexyl isononanoate, isotridecyl isononanoate, isononyl isononanoate or isodecyl neopentanoate can be used, and preferably isotridecyl isononanoate can be used.

The content of the oil agent having an expansion coefficient of 0.065%/° C. or less is preferably 10-50 wt %, more preferably 10-40 wt %, and most preferably 10-30 wt %.

In addition, the expansion coefficient of the oil agent having an expansion coefficient of 0.065%/° C. or less is preferably 0.060%/° C. or less, and more preferably 0.055%/° C. or less.

In the present invention, the oil agent includes an oil agent having a refractive index of 1.460 or more at 20° C. and an oil agent having an expansion coefficient of 0.065%/° C. or less, but it may also include other oil agents.

As the other oil agents, without limitation, the following can be used: isostearyl isostearate, dipentaerythrityl hexaisononanoate, hexyldecyl isostearate, isostearyl alcohol, decyltetradecanol, ethylhexyl hydroxystearate, isostearic acid, octyldodecyl myristate, isocetyl stearate, octyldodecanol, squalane, isocetyl myristate, isostearyl alcohol, glyceryl tri(caprylate/caprate), trimethylpropane triethylhexanoate, hexyldecanol, ethyl isostearate, ethylhexyl palmitate, bisethoxydiglycol succinate, isobutyl isostearate, isostearyl neopentanoate, neopentyl glycol dicaprate, triethylhexanoin, isopropyl isostearate, hexyldecyl ethylhexanoate, diethylhexyl succinate, cetyl ethylhexanoate, neopentyl glycol diisononanoate, isodecyl isononanoate, neopentyl glycol diethylhexanoate, hexyl laurate, isopropyl palmitate, isononyl isononanoate, isopropyl myristate, diisobutyl adipate, isodecyl neopentanoate, dimethicone.

As the transparent gelling agent in the present invention, without limitation, an amino-acid based gelling agent including dibutyl lauroyl glutamide (GP-1) and/or dibutyl ethylhexanoyl glutamide (EB-21), etc., or a polyamide resin can be used; preferably, an amino-acid based gelling agent including dibutyl lauroyl glutamide (GP-1) and/or dibutyl ethylhexanoyl glutamide (EB-21) and the like, and more preferably, dibutyl lauroyl glutamide (GP-1) and/or dibutyl ethylhexanoyl glutamide (EB-21) can be used.

In the case of containing dibutyl lauroyl glutamide (GP-1) and dibutyl ethylhexanoyl glutamide (EB-21), as long as the required amount of the oil agent as an oily solid cosmetic is contained, a transparent oily cosmetic exhibiting intended effects and having high storage stability can be produced.

In the case of containing dibutyl lauroyl glutamide (GP-1), its content is, relative to the entire cosmetic, preferably 1.0-10.0 wt %, more preferably 2.0-8.0 wt %, and most preferably 2.0-7.0 wt %.

In the case of containing dibutyl ethylhexanoyl glutamide (EB-21), its content is, relative to the entire cosmetic, preferably 0.5-10.0 wt %, more preferably 0.5-7.0 wt %, and most preferably 0.5-5.0 wt %.

In the case of containing dibutyl lauroyl glutamide (GP-1) and dibutyl ethylhexanoyl glutamide (EB-21), their blending ratio is determined from the viewpoint of transmittance; and the blending ratio (GP-1:EB-21) is preferably 75:25 to 25:75, more preferably 75:25 to 50:50. A cosmetic having high transparency can be produced by using a blending ratio within this range.

In the present invention, it is possible to prepare the gelling agent under mild conditions by using a solubilizing agent. As the solubilizing agent, without limitation, octyldodecanol, cetanol, and a higher fatty acid such as isostearic acid, etc. can be used, and preferably a higher fatty acid such as isostearic acid or octyldodecanol, and particularly preferably isostearic acid can be used. From the viewpoint of transparency and convenience, it is particularly preferable to use a higher fatty acid including isostearic acid.

The content of the solubilizing agent is preferably 5.0-30.0 wt %, more preferably 5.0-20.0 wt %, and most preferably 5.0-17.0 wt %.

In the present invention, the ingredient ratio in wt % between the oil agent having a refractive index of 1.460 or more at 20° C. and the oil agent having an expansion coefficient of 0.065 or less is preferably 10:1 to 1:1.

The cosmetic of the present invention may comprise various additives without limitation.

Various additives refer to any known various substances commonly used in cosmetics in general, which include preservatives, anti-inflammatory agents, antibacterial agents, antioxidants, ultraviolet absorbers, antiperspirants, vitamins, fragrances, colorants, ornamental agents such as pearlizing agent, whitening agents, anti-aging agents, other oil soluble drugs, and other oil soluble ingredients.

The present invention has been described in detail based on preferred embodiments; however, the present invention is not limited to these embodiments, and each constituent may be replaced with an arbitrary one that can exhibit a similar function, or an arbitrary constituent can be added.

Stick-type sun care cosmetics of Examples 1 to 12, Comparative Examples 1 to 7, and Examples 13 to 15 were prepared according to the following formulation, then the transmittance, bleeding test and usability were evaluated. Ingredient (A) is dibutyl lauroyl glutamide, ingredient (B) is dibutyl ethylhexanoyl glutamide, ingredient (C) is isostearic acid, ingredient (D) is an oil agent having a refractive index of 1.460 or more at 20° C., and ingredient (E) is an oil agent having an expansion coefficient of 0.065 or less.

Transmittance was measured in the absorption wavelength range of 350-800 nm, using a spectrometer V-650 from JASCO Corporation, and the average value at 380-750 nm was taken as the transmittance (%) of the solid cosmetic. In addition, when the transmittance was 60% or more, good transparency was visually confirmed. In the bleeding test, a hole having a diameter of 1 mm and a depth of 10 mm was formed in a plastic cuvette, the sample was left in a thermostatic chamber at 45° C. for one month, and its appearance was evaluated visually at room temperature (25° C.) after 24 hours. In addition, the usability was evaluated in terms of ease of spreading (spreadability) and no stickiness, using a 4-stage sensory evaluation by 10 expert panelists (5 panelists for each item). Evaluation was made according to the following criteria.

Spreadability to the Skin or Hair

◎: All five panelists recognized that spreadability to the skin or hair was good ○: Four panelists recognized that spreadability to the skin or hair was good Δ: Two to three panelists recognized that spreadability to the skin or hair is good X: One or less panelist recognized that spreadability to skin or hair was good No Stickiness to the Skin or Hair ◎: All five panelists recognized that there was no stickiness to the skin or hair ○: Four panelists recognized that there was no stickiness to the skin or hair Δ: Two to three panelists recognized that there was no stickiness to the skin or hair X: One or less panelist recognized that there was no stickiness to the skin or hair

EXAMPLES

Examples 1 to 12

For the cosmetics comprising ingredients (A) to (E) and having the ingredient ratio (wt %) of ingredient (D) to ingredient (E) of between 10:1 and 1:1, transmittance, bleeding test and usability were evaluated.

TABLE 3

| Material name | Example 1 | 2 | 3 | 4 | 5 | 6 | 7 | 8 | 9 | 10 | 11 | 12 |
|---|---|---|---|---|---|---|---|---|---|---|---|---|
| Ingredient (A) Dibutyl lauroyl glutamide | 5.4 | 5.4 | 19.2 | 5.4 | 5.4 | 5.4 | 6.4 | 9.6 | 16 | 19.2 | 5.4 | 16 |
| Ingredient (B) Dibutyl ethylhexanoyl glutamide | 1.8 | 1.8 | 8.1 | 1.8 | 1.8 | 1.8 | 2.7 | 4.05 | 6.75 | 8.1 | 12.8 | 6.75 |
| Isostearic acid | 12.8 | 12.8 | 2.7 | 12.8 | 12.8 | 12.8 | 0.9 | 1.35 | 2.25 | 2.7 | 1.8 | 2.25 |
| Rheopearl KL2 (Dextrin palmitate) | — | — | — | — | — | — | — | — | — | — | — | — |
| Ingredient (C) 12-hydroxystearic acid (KF TRADING) | 5 | 5 | 5 | 5 | 5 | 5 | 10 | 10 | 5 | 5 | 5 | 5 |
| MCX (Uvinul MC80) | 5 | 5 | 5 | 5 | 5 | 5 | 5 | 5 | 5 | 5 | 5 | 5 |
| Octocrylene (Eusolex OCR) | 5 | 5 | 5 | 5 | 5 | 5 | 5 | 5 | 5 | 5 | 5 | 5 |
| Uvinul A Plus Granular | 5 | 5 | 5 | 5 | 5 | 5 | 5 | 5 | 5 | 5 | 5 | 5 |
| Aerosil R972 (Dimethyl silylated silica) | — | — | — | — | — | — | — | — | — | — | — | — |
| Ingredient (D) KAK TCIN (Refractive index: 1.479, Expansion coefficient: 0.078) | 30 | 30 | 20 | 20 | 40 | 45 | 35 | 50 | 30 | 35 | 30 | 45 |
| NDO (Refractive index: 1.440, Expansion coefficient: 0.085) | — | — | — | — | — | — | — | — | — | — | — | — |
| KAK PTI (Refractive index: 1.468, Expansion coefficient: 0.073) | — | — | — | — | — | — | — | — | — | — | — | — |
| Ingredient (E) Neolight 100P (Refractive index: 1.430, Expansion coefficient: 0.062) | — | 30 | 15 | — | — | — | — | — | — | — | 30 | 10 |
| Ingredient (E) KAK 139 (Refractive index: 1.445, Expansion coefficient: 0.053) | 30 | — | 15 | 10 | 20 | 15 | 30 | 10 | 25 | 15 | — | — |
| Total | 100 | 100 | 100 | 70 | 100 | 100 | 100 | 100 | 100 | 100 | 100 | 100 |
| Ratio of ingredient (D)/ingredient (E) | 1/1 = 1 | 1/1 = 1 | 1/1 = 1 | 2/1 = 2 | 2/1 = 2 | 3/1 = 3 | 7/6 = 1.17 | 5/1 = 5 | 6/5 = 1.2 | 7/3 = 2.33 | 1/1 = 1 | 9/2 = 4.5 |
| Transmittance (%) If the transmittance is 60% or more, transparency by visual observation is good | 75 | 63 | 68 | 66 | 69 | 71 | 70 | 77 | 65 | 66 | 61 | 64 |
| Bleeding test using cuvette (45° C., 1 mo.) (With a hole) | No bleeding | No bleeding | No bleeding | No bleeding | No bleeding | No bleeding | No bleeding | No bleeding | No bleeding | No bleeding | No bleeding | No bleeding |
| Usability (ease of spreading to the skin) | ◎ | ◎ | ◎ | ◎ | ◎ | ◎ | ◎ | ○ | ◎ | ◎ | ◎ | ◎ |
| Usability (no stickiness after application) | ◎ | ◎ | ◎ | ◎ | ◎ | ○ | ◎ | ○ | ◎ | ◎ | ◎ | ◎ |

Comparative Examples 1 to 7

Stick-type sun care cosmetics were prepared by the following formulation of Comparative Examples 1 to 7, and transmittance, bleeding test and usability were evaluated.

TABLE 4

| Material name | Comparative Example | | | | | | |
|---|---|---|---|---|---|---|---|
| | 1 | 2 | 3 | 4 | 5 | 6 | 7 |
| Ingredient (A) Dibutyl lauroyl glutamide | 5.4 | 5.4 | 19.2 | 5.4 | 5.4 | 5.4 | 6.4 |
| Ingredient (B) Dibutyl ethylhexanoyl glutamide | 1.8 | 1.8 | 8.1 | 1.8 | 1.8 | 1.8 | 2.7 |
| Isostearic acid | 12.8 | 12.8 | 12.8 | 12.8 | 12.8 | 12.8 | 0.9 |
| Rheopearl KL2 (Dextrin palmitate) | — | — | 2.5 | — | — | 2.5 | — |
| Ingredient (C) 12-hydroxystearic acid (KF TRADING) | 5 | 5 | — | 5 | — | — | — |
| MCX (Uvinul MC80) | 5 | 5 | 5 | 5 | 5 | 5 | 5 |
| Octocrylene (Eusolex OCR) | 5 | 5 | 5 | 5 | 5 | 5 | 5 |
| Uvinul A Plus Granular | 5 | 5 | 5 | 5 | 5 | 5 | 5 |
| Aerosil R972 (Dimethyl silylated silica) | — | — | 2.5 | — | — | 2.5 | — |
| Ingredient (D) KAK TCIN (Refractive index: 1.479, Expansion coefficient: 0.078) | — | — | 60 | 60 | 65 | 30 | 30 |
| NDO (Refractive index: 1.440, Expansion coefficient: 0.085) | 30 | — | — | — | — | — | — |
| KAK PTI (Refractive index: 1.468, Expansion coefficient: 0.073) | 30 | — | — | — | — | — | — |
| Risocast IOHS (Refractive index: 1.456, Expansion coefficient: 0.111) | — | — | — | — | — | — | 30 |
| Ingredient (E) Neolight 100P (Refractive index: 1.430, Expansion coefficient: 0.062) | — | — | — | — | — | — | — |
| Ingredient (E) KAK 139 (Refractive index: 1.445, Expansion coefficient: 0.053) | — | 60 | — | — | — | 30 | — |
| Total | 100 | 100 | 100 | 70 | 100 | 100 | 100 |
| Ratio of ingredient (D)/ingredient (E) | — | — | — | — | — | 1/1 = 1 | — |
| Transmittance (%) | 33 | 45 | 42 | 82 | 90 | 51 | 80 |
| If the transmittance is 60% or more, transparency by visual observation is good | Poor Transparency | Poor Transparency | Poor Transparency | Good Transparency | Good Transparency | Poor Transparency | Good Transparency |
| Bleeding test using cuvette (45° C., 1 mo.) (With a hole) | No bleeding | No bleeding | Very slight bleeding | Very slight bleeding | Slight bleeding | Very slight bleeding | No bleeding |
| Usability (ease of spreading to the skin) | ○ | ○ | X | ○ | Δ | Δ | Δ |
| Usability (no stickiness after application) | Δ | Δ | ○ | Δ | Δ | ○ | Δ |

When the oil agent having a refractive index of 1.460 or more at 20° C. [ingredient (D)] is not contained, both of the Comparative Example 1 containing an oil agent having an expansion coefficient of 0.065 or less [ingredient (E)] and Comparative Example 2 not containing ingredient (E) did not show bleeding, but the transparency was poor. In Comparative Examples 3 to 5 and 7 which contained ingredient (D) with no ingredient (E), even though the transparency was good, they showed bleeding.

In Examples 13 to 15, cosmetics having a ratio of ingredient (D) to ingredient (E) of greater than 1 were prepared, and transmittance, bleeding test and usability were evaluated.

TABLE 5

| Example 13. Hair styling chic | (wt %) |
|---|---|
| 1. Ingredient (A) Dibutyl lauroyl glutamide | 6.75 |
| 2. Ingredient (B) Dibutyl ethylhexanoyl glutamide | 2.25 |
| 3. Isostearic acid Product name: Isostearic acid EX, Kokyu Alcohol Kogyo Co., Ltd. | 16.0 |
| 4. Ingredient (C) 12-hydroxystearic acid | 3.0 |
| 5. Ingredient (D) Tricyclodecanemethyl isononanoate Product name: KAK TCIN, Kokyu Alcohol Kogyo Co., Ltd. | 64.9 |
| 6. Ingredient (E) isodecyl Neopentanoate Product name: Neolight 100P, Kokyu Alcohol Kogyo Co., Ltd. | 7.0 |

TABLE 5-continued

| Example 13. Hair styling chic | (wt %) |
|---|---|
| 7. Perfume | 0.1 |
|  | 100.00 |
| Ratio of ingredient (D)/(E) | 64.9/7.0 = 9.7 |
| Bleeding test | No bleeding |
| Transmittance | 73% |
| Usability (spreadability) | Good |
| Usability (no stickiness) | No |

TABLE 6

| Example 14. Transparent lip gloss | (wt %) |
|---|---|
| 1. Ingredient (A) Dibutyl lauroyl glutamide | 9.60 |
| 2. Ingredient (B) Dibutyl ethylhexanoyl glutamide | 4.05 |
| 3. Isostearic acid<br>Product name: Isostearic<br>acid EX, Kokyu Alcohol Kogyo Co., Ltd. | 1.35 |
| 4. Ingredient (C) 12-hydroxystearic acid | 10.0 |
| 5. Ingredient (D) Tricyclodecanemethyl isononanoate<br>Product name: KAK TCIN, Kokyu<br>Alcohol Kogyo Co., Ltd. | 41.0 |
| 6. Ingredient (E) Isononyl isononanoate<br>(expansion coefficient: 0.057)<br>Product name: KAK99, Kokyu<br>Alcohol Kogyo Co., Ltd. | 7.0 |
| 7. Ingredient (D) Pentaerythrityl<br>tetraisostearate<br>Product name: KAK PTI,<br>Kokyu Alcohol Kogyo Co., Ltd. | 1.0 |
| 8. Hydrogenated castor oil dimer dilinoleate<br>Product name: Risocast DA-H, Kokyu<br>Alcohol Kogyo Co., Ltd. | 1.0 |
| 9. Hydrogenated polyisobuten | 25.0 |
|  | 100.00 |
| Ratio of ingredient (D)/(E) | 67.0/7.0 = 9.57 |
| Bleeding test | No bleeding |
| Transmittance | 81% |
| Usability (spreadability) | Good |
| Usability (no stickiness) | No |

TABLE 7

| Example 15. Transparent lipstick | (wt %) |
|---|---|
| 1. Ingredient (A) Dibutyl lauroyl glutamide | 5.4 |
| 2. Ingredient (B) Dibutyl ethylhexanoyl glutamide | 1.8 |
| 3. Isostearic acid<br>Product name: Isostearic acid EX,<br>Kokyu Alcohol Kogyo Co., Ltd. | 12.80 |
| 4. Ingredient (C) 12-hydroxystearic acid | 7.5 |
| 5. Ingredient (D) Tricyclodecanemethyl isononanoate<br>Product name: KAK TCIN, Kokyu<br>Alcohol Kogyo Co., Ltd. | 45.5 |
| 6. Ingredient (D) Diisostearyl malate<br>Product name: Haimalate DIS, Kokyu<br>Alcohol Kogyo Co., Ltd. | 3.0 |
| 7. Ingredient (D) Polyglyceryl-2 diisostearate<br>Product name: Risorex PGIS21,<br>Kokyu Alcohol Kogyo Co., Ltd. | 5.0 |
| 8. Ingredient (E) Isotridecyl isononanoate<br>(expansion coefficient: 0.053)<br>Product name: KAK 139, Kokyu<br>Alcohol Kogyo Co., Ltd. | 10.0 |
| 9. Ingredient (E) Ethylhexyl isononanoate<br>(expansion coefficient: 0.054)<br>Product name: ES108109, Kokyu<br>Alcohol Kogyo Co., Ltd. | 5.0 |

TABLE 7-continued

| Example 15. Transparent lipstick | (wt %) |
|---|---|
| 10. Ingredient (D) (Diglycerin/<br>dilinoleate/hydroxystearate) copolymer<br>Product name: Risocast HSDA, Kokyu<br>Alcohol Kogyo Co., Ltd. | 1.0 |
| 11. Ingredient (D) Trimethylolpropane triisostearate<br>Product name: KAK TTI, Kokyu<br>Alcohol Kogyo Co., Ltd. | 3.0 |
|  | 100.0 |
| Ratio of ingredient (D)/(E) | 52.5/15.0 = 3.83 |
| Bleeding test | No bleeding |
| Transmittance | 64% |
| Usability (spreadability) | Good |
| Usability (no stickiness) | No |

The cosmetics of Examples 13 to 15 showed satisfactory results in all of the transmittance, bleeding test and usability.

INDUSTRIAL APPLICABILITY

In the present invention, by using a transparent gelling agent, an oil agent having a refractive index of 1.460 or more at 20° C., and an oil agent having an expansion coefficient of 0.065%/° C. or less in combination, it is possible to provide a transparent solid cosmetic with no bleeding.

The invention claimed is:

1. A transparent oily solid cosmetic comprising transparent gelling agents which comprise dibutyl lauroyl glutamide and dibutyl ethylhexanoyl glutamide; an oil agent having a refractive index of 1.460 or more at 20° C.; an oil agent selected from the group consisting of ethylhexyl isononanoate, isotridecyl isononanoate, isononyl isononanoate and isodecyl neopentanoate; isostearic acid, wherein the content of isostearic acid is 5.0-30.0 wt %; and 12-hydroxystearic acid, wherein the content of 12-hydroxystearic acid is 2.0-10.0 wt %.

2. The transparent oily solid cosmetic according to claim 1, wherein the content of dibutyl lauroyl glutamide is 2.0-7.0 wt %.

3. The transparent oily solid cosmetic according to claim 1, wherein the content of dibutyl ethylhexanoyl glutamide is 0.5-5.0 wt %.

4. The transparent oily solid cosmetic according to claim 1, wherein the content of the oil agent having a refractive index of 1.460 or more at 20° C. is 20-80 wt %.

5. The transparent oily solid cosmetic according to claim 1, wherein the content of the oil agent selected from the group consisting of ethylhexyl isononanoate, isotridecyl isononanoate, isononyl isononanoate and isodecyl neopentanoate is 10-50 wt %.

6. The transparent oily solid cosmetic according to claim 1, wherein the oil agent having a refractive index of 1.460 or more at 20° C. is tricyclodecanemethyl isononanoate.

7. The transparent oily solid cosmetic according to claim 1, wherein the oil agent selected from the group consisting of ethylhexyl isononanoate, isotridecyl isononanoate, isononyl isononanoate or isodecyl neopentanoate having an expansion coefficient of 0.065 or less is isotridecyl isononanoate or isodecyl neopentanoate.

8. The transparent oily solid cosmetic according to claim 1, wherein the ingredient ratio in wt % between the oil agent having a refractive index of 1.460 or more at 20° C. and the oil agent selected from the group of ethylhexyl isononanoate, isotridecyl isononanoate, isononyl isononanoate or isodecyl neopentanoate is from 10:1 to 1:1.

* * * * *

UNITED STATES PATENT AND TRADEMARK OFFICE
CERTIFICATE OF CORRECTION

PATENT NO. : 10,792,235 B2
APPLICATION NO. : 15/823688
DATED : October 6, 2020
INVENTOR(S) : Takayuki Omura et al.

Page 1 of 1

It is certified that error appears in the above-identified patent and that said Letters Patent is hereby corrected as shown below:

In the Claims

Claim 7, Column 14, Line 52, should read:
7. The transparent oily solid cosmetic according to claim 1, wherein the oil agent selected from the group consisting of ethylhexyl isononanoate, isotridecyl isononanoate, isononyl isononanoate or isodecyl neopentanoate is isotridecyl isononanoate or isodecyl neopentanoate.

Signed and Sealed this
First Day of December, 2020

Andrei Iancu
*Director of the United States Patent and Trademark Office*